US009034831B2

(12) United States Patent
Chen et al.

(10) Patent No.: US 9,034,831 B2
(45) Date of Patent: May 19, 2015

(54) PHARMACEUTICAL COMPOSITION FOR A HEPATITIS C VIRAL PROTEASE INHIBITOR

(75) Inventors: Feng-Jing Chen, Danbury, CT (US); Robert J. Schwabe, Stamford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 567 days.

(21) Appl. No.: 12/830,771

(22) Filed: Jul. 6, 2010

(65) Prior Publication Data

US 2011/0160149 A1 Jun. 30, 2011

Related U.S. Application Data (60) Provisional application No. 61/223,507, filed on Jul. 7, 2009.

(51) Int. Cl.

| A61K 38/06 | (2006.01) |
|---|---|
| A61K 31/427 | (2006.01) |
| A61K 9/107 | (2006.01) |
| A61K 9/48 | (2006.01) |
| A61K 47/10 | (2006.01) |
| A61K 47/12 | (2006.01) |
| A61K 47/14 | (2006.01) |
| A61K 47/44 | (2006.01) |

(52) U.S. Cl.
CPC .............. *A61K 31/427* (2013.01); *A61K 9/1075* (2013.01); *A61K 9/4858* (2013.01); *A61K 47/10* (2013.01); *A61K 47/12* (2013.01); *A61K 47/14* (2013.01); *A61K 47/44* (2013.01)

(58) Field of Classification Search
None
See application file for complete search history.

(56) References Cited

U.S. PATENT DOCUMENTS

| 5,329,976 | A | 7/1994 | Haber et al. | |
|---|---|---|---|---|
| 6,268,207 | B1 | 7/2001 | Bailey | |
| 6,323,180 | B1 | 11/2001 | Llinas-Brunet et al. | |
| 6,828,301 | B2 * | 12/2004 | Chen et al. | 514/4.3 |
| 7,157,424 | B2 | 1/2007 | Chen et al. | |
| RE40,525 | E | 9/2008 | Llinas-Brunet et al. | |
| 7,514,557 | B2 | 4/2009 | Busacca et al. | |
| 7,585,845 | B2 | 9/2009 | Llinas-Brunet et al. | |
| 7,642,235 | B2 | 1/2010 | Llinas-Brunet et al. | |
| 7,939,667 | B2 | 5/2011 | Llinas-Brunet et al. | |
| 2003/0153614 | A1 | 8/2003 | Joshi-Hangal et al. | |
| 2004/0033959 | A1 | 2/2004 | Chen et al. | |
| 2004/0229777 | A1 | 11/2004 | Cerreta et al. | |
| 2005/0020503 | A1 * | 1/2005 | Llinas-Brunet et al. | 514/18 |
| 2005/0075279 | A1 | 4/2005 | Llinas-Brunet et al. | |
| 2005/0080005 | A1 | 4/2005 | Llinas-Brunet et al. | |
| 2005/0142225 | A1 | 6/2005 | Kysilka et al. | |
| 2005/0209135 | A1 | 9/2005 | Busacca et al. | |
| 2005/0267151 | A1 | 12/2005 | Busacca et al. | |
| 2006/0134203 | A1 | 6/2006 | Ambuhl et al. | |
| 2006/0276406 | A1 | 12/2006 | Gupta et al. | |
| 2008/0177029 | A1 | 7/2008 | Busacca et al. | |
| 2012/0101049 | A1 | 4/2012 | Chen et al. | |

FOREIGN PATENT DOCUMENTS

| WO | 2004103996 A1 | 12/2004 |
|---|---|---|
| WO | 2005095403 | 10/2005 |
| WO | 2005116054 A1 | 12/2005 |
| WO | 2009099596 A2 | 8/2009 |
| WO | 2010033444 A1 | 3/2010 |
| WO | 2010059667 A1 | 5/2010 |
| WO | 2011005646 A2 | 1/2011 |

OTHER PUBLICATIONS

International Search report, Form PCT/ISA/210 for application PCT/US2010/040734, date of mailing Oct. 25, 2011.
International Preliminary Report on Patentability, Form PCT/IB/373, and Written Opinion, Form PCT/ISA/237, for application PCT/US2010/040734, date of issue Jan. 10, 2012.
Beaulieu et al., Synthesis of (1R,2S) -1-Amino-2-vinylcyclopropanecarboxylic Acid Vinyl-ACCA) Derivatives: Key Intermediates for the Preparation of Inhibitors of the Hepatitis C Virus NS3 Protease, Journal of Organic Chemistry, vol. 70, No. 15, Jan. 1, 2005, pp. 5869-5879.
Marti-Mestres et al., Main Surfactants Used in the Pharmaceutical Field, Drugs and Pharmaceticals Sciences, 2000, 105, pp. 1-18.

* cited by examiner

*Primary Examiner* — Karlheinz R Skowronek
*Assistant Examiner* — Lianko Garyu
(74) *Attorney, Agent, or Firm* — Michael P. Morris; Philip I. Datlow (57) ABSTRACT

Disclosed is a pharmaceutical composition of a hepatitis C viral protease inhibitor which is suitable for oral administration via a liquid- or semi-solid-filled capsule and methods of using this composition for inhibiting the replication of the hepatitis C virus (HCV) and for the treatment of an HCV infection. The liquid- or semi-solid pharmaceutical composition of the present invention comprises a compound of formula I, or a pharmaceutically acceptable salt thereof, together with one or more pharmaceutically acceptable lipids and hydrophilic surfactants.

19 Claims, 3 Drawing Sheets

PHARMACEUTICAL COMPOSITION FOR A HEPATITIS C VIRAL PROTEASE INHIBITOR

FIELD OF THE INVENTION

The present invention relates in general to a pharmaceutical composition of a hepatitis C viral protease inhibitor, methods of using this composition for inhibiting the replication of the hepatitis C virus (HCV) and for the treatment of an HCV infection.

BACKGROUND OF THE INVENTION

The following Compound (1):

(1)

(hereinafter "Compound (1)" or a "compound of formula (1)") is known as a selective and potent inhibitor of the HCV NS3 serine protease. Compound (1) falls within the scope of the acyclic peptide series of HCV inhibitors disclosed in U.S. Pat. No. 6,323,180 and U.S. Pat. No. 7,514,557; and U.S. Pat. No. 7,585,845. Compound (1) is disclosed specifically as Compound #1055 in U.S. Pat. No. 7,585,845, and as Compound #1008 in U.S. Pat. No. 7,514,557. Compound (1) can be prepared according to the procedures found in the above-cited references, which are herein incorporated by reference in their entirety. Preferred forms of Compound (1) include the crystalline forms, in particular the crystalline sodium salt form, which can be prepared as described in the examples section herein.

Compound (1) may also be known by the following alternate depiction of its chemical structure, which is equivalent to the above-described structure:

wherein B is

;

$L^0$ is MeO—; $L^1$ is Br; and $R^2$ is

.

A common problem among protease inhibitors is that these compounds are lipophilic and have low aqueous solubility. Because of the poor aqueous solubility, conventional solid and liquid pharmaceutical preparations containing these inhibitors may not be absorbed by the patient in a satisfactory manner. Of the various factors that can affect the bioavailability of a drug when administered orally, (which include aqueous solubility, drug absorption through the gastrointestinal tract, dosage strength and first pass effect), aqueous solubility is often found to be among the most important factors. Poorly water soluble compounds often exhibit either erratic or incomplete absorption in the digestive tract, and thus produce a less than desirable response.

Compound (1) is zwitterionic and is capable of forming salts with strong acids and bases. Attempts to identify salts of such compound in solid forms, which would substantially improve aqueous solubility and therefore bioavailability, have not been successful. Thus, there is a need in the art for pharmaceutical compositions of Compound (1) having improved bioavailability.

Methods of formulating certain lipophilic macrocyclic compounds into pharmaceutical formulations have been previously reported. For example, Cavanak, U.S. Pat. No. 4,388,307, discloses the preparation of emulsified formulations of commercially available cyclosporins, and Hauer et. al, U.S. Pat. No. 5,342,625, and Meizner et al. WO 93/20833 disclose the preparation of cyclosporin microemulsions and microemulsion pre-concentrates. Komiya et. al, U.S. Pat. No.

5,504,068, further to discloses the preparation of an enhanced topical formulations of cyclosporin.

Examples of "self-emulsifying" formulations of lipophilic compounds include Lipari et al, WO 96/36316, which discloses a self-emulsifying pre-concentrate comprising a lipophilic compound, d-alpha-tocopheryl polyethylene glycol 1000 succinate (TPGS) and a lipophilic phase. Gao et al., U.S. Pat. No. 6,121,313 discloses a self-emulsifying formulation of a pyranone protease inhibitor comprising the pyranone compound, a mixture of mono- and di-glycerides, one or more solvents and one or more surfactants, and Gao et al, U.S. Pat. No. 6,231,887 B1 discloses a self-emulsifying formulation of a pyranone protease inhibitor comprising the pyranone compound, an amine, one or more solvents and one or more surfactants. Crison et al. U.S. Pat. No. 5,993,858 discloses a self-microemulsifying excipient formulation which comprises an emulsion including an oil or other lipid material, a surfactant and a hydrophilic co-surfactant.

Patel et al. U.S. Pat. Nos. 6,294,192 and 6,451,339 disclose compositions for delivery of a hydrophobic therapeutic agent comprising a carrier formed from a combination of a hydrophilic surfactant and a hydrophobic surfactant. Aylwin et al. U.S. Pat. No. 6,652,880 discloses a liquid pharmaceutical composition wherein the active is dissolved in a liquid vehicle comprising a glyceride of a long chain fatty acid and a lipophilic surfactant.

A self-emulsifying drug delivery system (SEDDS) has also been developed for certain anti-HCV compounds, as described in U.S. Pat. Nos. 6,828,301 and 7,157,424 and U.S. Patent Application Publication No. 2004/0033959. However, there remains a need in the art for a pharmaceutical formulation of Compound (1) that is sufficiently optimized, stable and bioavailable.

BRIEF SUMMARY OF THE INVENTION

The present invention overcomes the aforementioned problems by providing a lipid-based pharmaceutical composition of Compound (1), suitable for oral administration via a liquid- or semi-solid-filled capsule. The lipid-based pharmaceutical compositions of the present invention constitute a type of self-emulsifying drug delivery system (hereinafter "SEDDS"), and they exhibit acceptable stability and bioavailability and are therefore particularly suited for the therapeutic delivery of Compound (1).

The pharmaceutical compositions of the present invention all comprise Compound (1), or a pharmaceutically acceptable salt thereof, together with one or more pharmaceutically acceptable lipids and hydrophilic surfactants. The compositions of the present invention may optionally include one or more additional ingredients, e.g., pharmaceutically acceptable hydrophilic solvents, solidifying agents, antioxidants, etc., as will be discussed in more detail below. The pharmaceutical compositions are liquid or semi-solid and are preferably encapsulated in a capsule for oral administration.

Another important aspect of the present invention involves a method of treating a hepatitis C viral infection in a mammal by administering to the mammal a therapeutically effective amount of a pharmaceutical composition of the present invention.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The term "about" means within 20%, preferably within 10%, and more preferably within 5% of a given value or range. For example, "about 10%" means from 8% to 12%, preferably from 9% to 11%, and more preferably from 9.5% to 10.5%. When the term "about" is associated with a range of values, e.g., "about X to Y %", the term "about" is intended to modify both the lower (X) and upper (Y) values of the recited range. For example, "about 0.1 to 10%" is equivalent to "about 0.1% to about 10%".

All percentages recited for amounts of ingredients in the compositions are percentages by weight with respect to the whole composition.

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "semi-solid" means a material that is neither solid (elastic behavior) nor liquid (viscous behavior) and possesses the characteristics of both viscosity and elasticity. Examples of semi-solid materials include gels, ointments, creams, and highly viscous liquids.

The terms "treating" or "treatment" mean the treatment of a hepatitis C viral infection in a patient, and include:
(i) preventing the hepatitis C viral infection from occurring in a patient, in particular, when such patient is predisposed to such disease-state but has not yet been diagnosed as having it;
(ii) inhibiting or ameliorating the hepatitis C viral infection, i.e., arresting or slowing its development; or
(iii) relieving the hepatitis C viral infection, i.e., causing regression or cure of the disease-state.

The term "therapeutically effective amount" means an amount of a compound according to the invention which, when administered to a patient in need thereof, is sufficient to effect treatment of a hepatitis C viral infection. Such a therapeutically effective amount can be determined routinely by one of ordinary skill in the art having regard to their own knowledge, the prior art, and this disclosure.

Preferred Embodiments of the Invention

As a general embodiment of the present invention, the pharmaceutical composition comprises a compound of formula (1) or a pharmaceutically acceptable salt thereof, one or more pharmaceutically acceptable lipids and one or more pharmaceutically acceptable hydrophilic surfactants. In a more specific embodiment, the pharmaceutical composition consists essentially of a compound of formula (1) or a pharmaceutically acceptable salt thereof, one or more pharmaceutically acceptable lipids and one or more pharmaceutically acceptable hydrophilic surfactants.

Compound (1)

The Compound (1) can be used in its free form or in the form of its pharmaceutically acceptable salt. The term "pharmaceutically acceptable salt" means a salt of a compound (1) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use.

The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19 and U.S. Pat. No. 7,585,845. The various salts listed in U.S. Pat. No. 7,585,845 are herein incorporated by reference.

A particularly preferred form of Compound (1) to be used in the composition of the present invention is the sodium salt form of Compound (1). Methods for manufacturing the crystalline sodium salt form are provided in the Examples section herein. The Compound (1) sodium salt could be crystalline, amorphous or mixtures thereof. It could be also a different polymorph from the current crystalline drug substance as herein described. The Compound (1) drug substance can be used directly as it is or it can be subject to an appropriate process to (1) reduce the extent of agglomeration of drug substance particles and/or (2) reduce the particle size distribution of the drug substance primary particles. The process could be sieving, deagglomeration, impact milling, jet milling or combinations thereof to reduce the mixing time of the bulk fill manufacturing for encapsulation.

The amount of the active ingredient of Compound (1) that may be present in the lipid-based system composition may vary widely or be adjusted widely depending on the intended route of administration, the potency of the particular active ingredient being used, the severity of the hepatitis C viral infection and the required concentration. In a particular embodiment, the compound of formula (1) is present in the lipid-based system in an amount of from about 1% to 50% by weight, preferably from about 5% to 30% by weight, more preferably from about 10% to 20% by weight.

Lipid Material

As is well known in the art, an empirical parameter commonly used to characterize the relative hydrophilicity and hydrophobicity of compounds is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 10.

Pharmaceutically acceptable lipids useful in the composition of the present invention include any lipophilic material having a hydrophilic-lipophilic balance ("HLB" value) of less than or equal to 10 (HLB≤10) within limited solubility in water. Examples of pharmaceutically acceptable lipids that are useful include a broad spectrum of water-immiscible materials such as, for example, fatty acids, medium or long chain mono-, di- or triglycerides, propylene glycol fatty acid esters, sorbitol fatty acid esters, water insoluble vitamins, and mixtures thereof. In a preferred embodiment, the pharmaceutically acceptable lipid is selected from: monoglycerides of caprylic and capric fatty acids, diglycerides of caprylic and capric fatty acids, and mixtures thereof (e.g. CAPMUL® MCM from Abitech Corp.).

The amount of lipid in the composition may vary over a wide range and the optimum amount for a particular composition will depend on the type and amount of other the other ingredients in the composition as can be determined by the skilled pharmaceutical technician. In general, however, the pharmaceutically acceptable lipid is present in an amount of from about 20% to 70% by weight, more preferably in an amount of from about 30% to 60% by weight, or in an amount of from about 40% to 50% by weight.

Hydrophilic Surfactant

To facilitate self-emulsification, the composition of the present invention includes a pharmaceutically acceptable hydrophilic surfactant having an HLB value of greater than or equal to 10 (HLB≥10) with good miscibility with water. Examples of pharmaceutically acceptable hydrophilic surfactants that are useful include polyethoxylated vegetable oils, polyethoxylated tocopherols, polyethoxylated sorbitol fatty acid esters (e.g. Tween 80), bile salts, lecithins and mixtures thereof. Preferred surfactants include tocopheryl polyethylene glycol succinate (Vitamin E TPGS), polyoxyl 40 hydrogenated castor oil (Cremophor RH40), and polyoxyl 35 castor oil (Cremophor EL), and mixtures thereof.

The amount of hydrophilic surfactants in the composition may also vary over a wide range and the optimum amount for a particular composition will depend on the type and amount of other the other ingredients in the composition as can be determined by the skilled pharmaceutical technician. The pharmaceutically acceptable hydrophilic surfactant is preferably present in an amount of up to about 70% by weight, preferably from about 20% to 50% by weight, more preferably from 25% to 35% by weight.

Hydrophilic Solvent

The composition of the present invention can optionally further comprise a pharmaceutically acceptable hydrophilic solvent to: (1) enhance the solubility of the active drug substance and prevent its precipitation out of the formulation, (2) reduce the mixing time of the bulk liquid fill composition during manufacturing for encapsulation into capsules and/or (3) improve the aqueous dispersibility of the formulation. Examples of hydrophilic solvents that can be used include, for example, propylene glycol, polypropylene glycol, polyethylene glycol, glycerol, ethanol, dimethyl isosorbide, glycofurol, propylene carbonate, dimethyl acetamide, water, or mixtures thereof. Preferred hydrophilic solvents include propylene glycol, polyethylene glycol (e.g., PEG 400), ethanol, water, and mixtures thereof.

The amount of solvent in the composition may also vary over a wide range and the optimum amount for a particular composition will depend on the type and amount of other the other ingredients in the composition as can be easily determined by the skilled worker. In general, however, the solvent(s) are present in an amount of up to about 30% by weight, preferably up to 15% by weight.

Solidifying Agent

The composition of the present invention can optionally further comprise a solidifying agent to convert the liquid formulation into a semi-solid after encapsulation in two-piece hard capsules (e.g., hard gelatin capsules and HPMC capsules). Examples of solidifying agents that can be used include polyethylene glycols, poloxamers, polyvinylpyrrolidones, polyvinylalcohols, cellulose derivatives, polyacrylates, polymethacrylates, sugars, polyols, and mixtures thereof. Specific preferred examples include high molecular weight PEGs including PEG3350, PEG6000, PEG8000, poloxamers or mixtures thereof. The inclusion of a solidifying agent is particularly useful for propylene glycol- or ethanol-containing compositions to reduce the activity of the gelatin plasticizer from migrating from the liquid fill into the capsule shell thereby improving the physical stability with respect to softening and deformation of the dosage form. On the other hand, this approach is also useful for PEG400-containing compositions to reduce the hygroscopicity of the fill and brittleness of the capsule. When used in the composition, the solidifying agent is preferably be present in an amount up to about 50% by weight, preferably about 1 to 20% by weight.

Optional Additional Ingredients

If desired, the compositions according to the present invention may further include conventional pharmaceutical additives as is necessary or desirable to obtain a suitable formulation, such as antioxidants, lubricants, disintegrants, preservatives, buffers, stabilizers, scavengers, thickening agents, coloring agents, sweetening agents, flavoring agents, fragrances, etc. Additional additives that may be useful in the compositions of the invention are disclosed in Llinas-Brunet et al., U.S. Pat. No. 6,323,180 B1.

In one preferred embodiment, the compositions according to the present invention further contain one or more antioxidants. Preferred antioxidants include, for example, ascorbic acid, sulfatide salts, citric acid, propyl gallate, dl-alpha-tocopherol, ascorbyl palmitate, BHT or BHA. If present, the antioxidant is generally present in an amount of from about 0.01% to 1% by weight.

In another preferred embodiment, the composition of the present invention can further comprise an active carbonyl (e.g., aldehydes, ketones) scavenger (e.g., amines including TRIS and meglumine) to reduce the cross-linking of gelatin capsules which might adversely affect the release of the formulation from the dosage form.

Stabilizers that may be used can include, e.g., some alkaline agents, including amines, which raise the apparent pH of the fill formulation.

Additional Preferred Embodiments

In additional embodiments, the composition of the present invention is characterized by not including (or having only limited quantities of) one or more classes of materials that may be typically included in pharmaceutical formulations. In the context of the descriptions below, the phrase "substantially free of" a certain material generally means that the formulation contains no more than a trace amount of the material, e.g. no more than 1% by weight, preferably no more than 0.5%, even more preferably no more than 0.1% by weight.

The composition of the present invention may be characterized by one or more of the following features:
(1) either substantially free of any amine compound, or not containing any amine compound;
(2) either substantially free of any alcohol compound, or not containing any alcohol compound;
(3) either substantially free of any triglyceride compound, or not containing any triglyceride;
(4) either substantially free of any glyceride of a long chain fatty acid, or not containing any such glyceride;
(5) either substantially free of any additional surfactant compound, or not containing any additional surfactant compound;

A particular embodiment of the composition according to the present invention is directed to a pharmaceutical composition, comprising (or consisting essentially of):
(a) about 5% to 30% by weight of a compound of formula (1) or a pharmaceutically acceptable salt thereof;
(b) about 30% to 60% by weight of a pharmaceutically acceptable lipid;
(c) about 20% to 50% by weight of a pharmaceutically acceptable hydrophilic surfactant;
(d) optionally up to about 30% by weight of a pharmaceutically acceptable hydrophilic solvent;

A further particular embodiment of the composition according to the present invention is directed to a pharmaceutical composition, comprising (or consisting essentially of):
(a) about 10% to 20% by weight of a compound of formula (1) or a pharmaceutically acceptable salt thereof;
(b) about 40% to 50% by weight of a pharmaceutically acceptable lipid;
(c) about 25% to 35% by weight of a pharmaceutically acceptable hydrophilic surfactant;
(d) about 5% to 15% by weight of a pharmaceutically acceptable hydrophilic solvent;

A further particular embodiment of the composition according to the present invention is directed to a pharmaceutical composition, comprising (or consisting essentially of):
(a) about 5% to 30% by weight of a compound of formula (1) or a pharmaceutically acceptable salt thereof;
(b) about 30% to 60% by weight of a pharmaceutically acceptable lipid selected from fatty acids, medium or long chain mono-, di- or triglycerides, propylene glycol fatty acid esters, sorbitol fatty acid esters, water insoluble vitamins, and mixtures thereof;
(c) about 20% to 50% by weight of a pharmaceutically acceptable hydrophilic surfactant selected from polyethoxylated vegetable oils, polyethoxylated tocopherols, polyethoxylated sorbitol fatty acid esters, bile salts, lecithins and mixtures thereof;
(d) optionally up to about 30% by weight of a pharmaceutically acceptable hydrophilic solvent selected from propylene glycol, polypropylene glycol, polyethylene glycol, glycerol, ethanol, dimethyl isosorbide, glycofurol, propylene carbonate, dimethyl acetamide, water, or mixtures thereof;

A further particular embodiment of the composition according to the present invention is directed to a pharmaceutical composition, comprising (or consisting essentially of):
(a) about 10% to 20% by weight of a compound of formula (1) as the sodium salt;
(b) about 40% to 50% by weight of a pharmaceutically acceptable lipid selected from monoglycerides of caprylic and capric fatty acids; diglycerides of caprylic and capric fatty acids, and mixtures thereof;
(c) about 25% to 35% by weight of a pharmaceutically acceptable hydrophilic surfactant selected from tocopheryl polyethylene glycol succinate, polyoxyl 40 hydrogenated castor oil, and polyoxyl 35 castor oil and mixtures thereof;
(d) about 5% to 10% by weight of a pharmaceutically acceptable hydrophilic solvent selected from propylene glycol, polyethylene glycol, ethanol, water, and mixtures thereof.

Manufacturing Method and Encapsulation

The composition of the present invention may be prepared in a conventional manner, for example, by a method comprising mixing together the liquid components, e.g., the pharmaceutically acceptable lipid(s), surfactant(s) and solvent(s); optionally heating the mixture obtained if necessary to sufficiently melt one or more of the components of the mixture; adding the compound of formula (1) to the resulting mixture and further mixing until all or substantially all of the compound of formula I is solubilized, e.g. until the solution is visually clear. This method of preparing the composition constitutes another aspect of the present invention.

The resulting fill solution is then formulated into the desired dosage form, for example, capsules including hard shell or softgel capsules (e.g., hard or soft gelatin capsules), by known manufacturing technology. Examples of soft gelatin capsules that can be used include those disclosed in EP 649651 B1 and U.S. Pat. No. 5,985,321.

In a particularly preferred embodiment, the composition of the present invention is encapsulated in soft elastic capsules, e.g. soft gelatin capsule and other non-animal based soft capsules. Since the composition can be substantially free of polar solvent, it can offer the advantage of using an off-the-shelf standard gel composition for the capsule shell or a straightforward development of a new gel for the capsule shell to minimize the development challenges and costs. Since a soft capsule can support a larger fill volume, the composition of the present invention will have the advantage of providing higher drug loading.

It is noted that the composition of the present invention can further comprise water inherent from the drug substance, excipients (in particular from surfactants and solvents which are hydrophilic in nature) and as generated during the encapsulation process. Particularly during the encapsulation of the fill formulation with soft gelatin capsules, large amounts of moisture can migrate into the fill formulation from the wet gelatin ribbons. It is important to remove any excessive moisture from the fill composition by using an appropriate drying process to avoid any precipitation and hydrolytic degradation of the drug substance and excessive softening of the capsule. Typically, the finished soft gelatin capsules of the present invention should comprise no more than 5% by weight and more preferably no more than 3% by weight of water in the fill formulation.

One of the important discoveries relating to the compositions of the present invention is that the solubility of Compound (1) sodium salt increases as the temperature decreases. This unexpected property offers a unique opportunity to improve the stability of the drug product by cold storage (e.g., refrigeration) without the concern of potential drug precipitation at lower temperature. As a result, the compositions of the present invention have an unexpected advantage in packaging development which allows for a broad range of packaging materials to be used.

Methods of Therapeutic Use

The compounds of formula (1) are effective as HCV protease inhibitors, and these compounds and pharmaceutical compositions comprising these compounds are therefore useful in inhibiting the replication of HCV and in the treatment of HCV infection in a mammal. Therefore, the present invention is also directed to treating a hepatitis C viral infection in a mammal by administering to the mammal a therapeutically effective amount of a pharmaceutical composition of the present invention.

Dosage levels of the compounds of formula (1) and various treatment regimens in the monotherapy for the prevention and treatment of HCV infection are as set forth in U.S. Pat. No. 7,585,845. As the skilled artisan will appreciate, however, lower dosages may be possible with the compositions of the present invention depending on the level of improvement in bioavailability. Combination therapy is also possible with one or more additional therapeutic or prophylactic agents as fully described by U.S. Pat. No. 7,585,845. The additional agent(s) may be combined with the compounds of this invention to create a single dosage form or, alternatively, these additional agent(s) may be separately administered to a mammal as part of a multiple dosage form. An appropriate therapeutically effective amount of the pharmaceutical composition to be administered can be determined routinely by one of ordinary skill in the art having regard to their own knowledge, the prior art, and this disclosure.

In order that this invention be more fully understood, the following examples of are set forth. These examples are for the purpose of illustrating embodiments of this invention, and are not to be construed as limiting the scope of the invention in any way.

Characteristics of the Drug Product

The lipid-based drug delivery system of the present invention was selected because of the lipophilic nature of Compound (1) sodium salt. Lipid-based SEDDS (self-emulsifying drug delivery system) formulations are able to overcome solubility-limited absorption. Since the drug substance is in solution in the dosage form and is to maintained in solution upon contact with aqueous media due to the self-emulsifying properties of the formulation, absorption is not dissolution rate-limited.

A liquid-filled soft gelatin capsule formulation according to the present invention has been developed for use in clinical trials. The important performance attributes include:
  bioavailability (rapid release during in vitro dissolution; comparable absorption in dogs to the previous powder for oral solution formulations)
  stability (demonstrated chemical and physical stability of the dosage form at ICH long-term storage conditions, 25° C./60% RH)
  manufacturability (batch sizes up to 25 kg feasible to support trial requirements)

Data is provided in the Examples section herein demonstrating the superior stability and bioavailability characteristics of the capsule formulation of the present invention.

The optical clarity of formulations of the present invention was observed visually and measured spectroscopically. The fill formulations were prepared according to Example 1 below (as well as corresponding vehicle and placebo formulations), and diluted to 100 times solutions in aqueous media. The absorbance of each solution was measured at 400 nm and 450 nm, using a purified water standard, and the detailed results are provided in the Examples section herein. The results demonstrate absorbances of the dispersions in the range of 2.36 to 2.99 at 400 nm 0.35 to 2.96 at 450 nm. Accordingly, an additional embodiment is directed to a pharmaceutical composition according to the present invention wherein upon dilution with an aqueous solution at an aqueous solution to composition ratio of 100:1 by weight, the composition forms an aqueous dispersion having an absorbance of more than about 1.0 at a wavelength of about 400 nm, and preferably more than about 2.0 at a wavelength of about 400 nm.

EXAMPLES

Three different liquid fill formulations were manufactured, two of which were encapsulated in softgel capsules (SGC) and one encapsulated in a hard-shell capsule (HSC).

Example 1

Softgel Capsule Formulation #1

The composition of the liquid fill formulation:

| Ingredient | Monograph | Functionality | % w/w |
|---|---|---|---|
| Compound (1) Na salt | | API | 15.0 |
| Mono-, Diglycerides of Caprylic/Capric Acid (Capmul ® MCM) | | Lipid | 46.3 |
| Polyoxyl 35 Castor Oil (Cremophor ® EL) | NF | Surfactant | 30.8 |
| Propylene Glycol | USP | Solvent | 7.7 |
| DL-α-tocopherol | USP | Anti-oxidant | 0.2 |
| Total | | | 100.0 |

Two specific soft-gel capsule drug product formulations were prepared according to the above general Formulation #1, a 40 mg product and a 120 mg product:

| Ingredient | Function | 40 mg mg/capsule | 120 mg mg/capsule |
|---|---|---|---|
| Compound (1) Na salt (milled) | Drug substance | 42.30[1] | 126.90[2] |
| Mono/Diglycerides of Caprylic/Capric Acid | Lipid phase | 130.57 | 391.70 |
| Polyoxyl 35 Castor Oil (NF) Macrogolglycerol Ricinoleate (Ph. Eur.) | Surfactant | 86.86 | 260.57 |
| Propylene Glycol | Solvent | 21.71 | 65.14 |
| Vitamin E (dl-alpha tocopherol) (USP) All-rac-alpha-tocopherol (Ph. Eur.) | Anti-oxidant | 0.56 | 1.69 |
| Nitrogen[3] | Processing aid | q.s. | q.s. |
| Total Fill Weight | | 282.00 | 846.00 |
| Soft Gelatin Capsule Shell | Shell | 280[4] | 590[5] |
| Wet Total Capsule Weight | | 562 | 1436 |
| Dry Total Capsule Weight | | 480 | 1250 |

[1] 42.30 mg of Compound (1) Na salt is equivalent to 40.0 mg of the active moiety.
[2] 126.90 mg of Compound (1) Na salt is equivalent to 120.0 mg of the active moiety.
[3] Nitrogen is used as a processing aid and does not appear in the final product.
[4] The approximate weight of the capsule shell before drying and finishing is 280 mg. The approximate weight of the capsule shell after drying and finishing is 198 mg.
[5] The approximate weight of the capsule shell before drying and finishing is 590 mg. The approximate weight of the capsule shell after drying and finishing is 404 mg.

Example 2

Softgel Capsule Formulation #2

The composition of the liquid fill formulation:

| Ingredient | Monograph | Functionality | % w/w |
|---|---|---|---|
| Compound (1) Na salt | | API | 15.0 |
| Mono-, Diglycerides of Caprylic/Capric Acid (Capmul ® MCM) | | Lipid | 42.4 |
| Polyoxyl 35 Castor Oil (Cremophor ® EL) | NF | Surfactant | 33.9 |
| Propylene Glycol | USP | Solvent | — |
| Oleic Acid | | Lipid | 8.5 |
| DL-α-tocopherol | USP | Anti-oxidant | 0.2 |
| Total | | | 100.0 |

A specific 150 mg soft-gel capsule drug product formulation was prepared according to the above general formula.

Example 3

Hard Shell Capsule Formulation #3

The composition of the liquid fill formulation:

| Ingredient | Monograph | Functionality | % w/w |
|---|---|---|---|
| Compound (1) Na salt | | API | 20.0 |
| Mono-, Diglycerides of Caprylic/Capric Acid (Capmul ® MCM) | | Lipid | 53.8 |
| Polyoxyl 35 Castor Oil (Cremophor ® EL) | NF | Surfactant | 23.0 |
| Propylene Glycol | USP | Solvent | 3.0 |
| DL-α-tocopherol | USP | Anti-oxidant | 0.2 |
| Total | | | 100.0 |

A specific 150 mg hard-shell capsule drug product formulation was prepared according to the above general formula.

Preparation of Formulations 1-3

The drug substance is jet-milled to remove large aggregates so that the mixing time for the bulk fill manufacturing will be consistent and reasonably short. The target particle size distribution of the drug substance is to reduce the x90 (v/v) to no more than 10 micron and the x98 (v/v) to no more than 20 micron as measured by Sympatec. All the excipients in the fill formulation are combined in a mixing vessel and mixed until uniform prior to adding the drug substance. After addition of the drug substance, mixing continues until the fill solution is clear by visual inspection. A nitrogen blanket over the fill solution is used throughout the preparation as a standard practice. The fill solution is passed through a filter to remove any extraneous particles. Encapsulation of the filtered bulk fill material in capsules is performed utilizing standard soft gelatin or hard gelatin capsule technology and in-process controls. Filled capsules are dried and then washed with a finishing/wash solution prior to packaging resulting in shiny, pharmaceutically elegant capsules.

Example 4

Chemical Stability Studies

Stability has been assessed on a prototype formulation of a higher strength capsule (150 mg, based on sodium salt) with the same relative quantities of fill excipients and a gel formulation as Formulation #1 (Example 1) and that is qualitatively the same as Formulation #1. No significant change in assay or impurity profile was noted after 12 months at 25° C./60% RH or 30° C./70% RH.

Example 5

Dissolution and Bioavailability Studies

Figure 1:
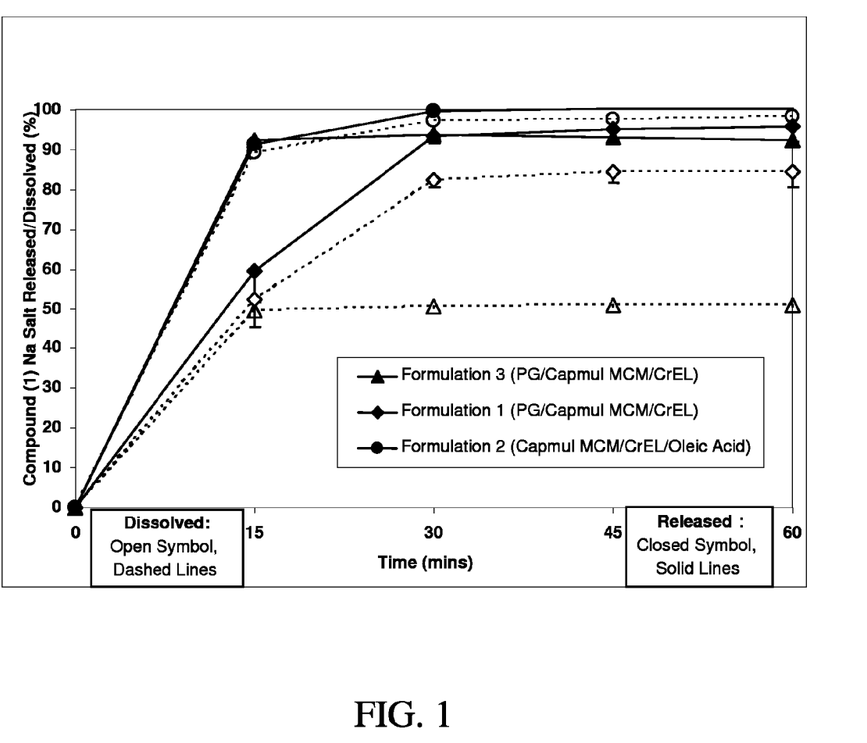
FIG. 1 shows the results of in vitro dissolution testing of three formulations according to the present invention, depicting the percent amount of Compound (1) Na salt released/dissolved as a function of time.

An in vitro dissolution method has been used to evaluate Formulations 1-3. The results demonstrate the release of the fill formulation from the capsule and the dispersion of the drug substance in the lipid-based self-emulsifying drug delivery system upon contact with aqueous media. See FIG. 1. The dissolution testing was conducted according to the following protocol: 2×150 mg capsules for each formulation; conducted in 500 ml pH 4.5 acetate buffer solution per vessel; 100 rpm, baskets, at 37° C.

Additionally, the bioavailability of the SEDDS formulation capsules has been demonstrated in vivo in dogs, showing comparable absorption to earlier "powder-in-bottle" oral solution formulations which have been shown to result in sufficient exposure in human clinical studies. The protocol and results from these in vivo studies are provided below.

Five-Way Crossover Formulation Study in Beagle Dogs

Animals/Design: 6 male beagle dogs in a cross-over design. There was one week washout between visits 1 and 2, & visits 3 and 4. There was a two-week washout between visits 2 and 3 & visits 4 and 5.

Pretreatment: Pentagastrin @ 6 μg/kg IM one hour before dosing with formulations.

Fed Status: Fasted overnight (fed after 4 hr timepoint)

Formulations:

A—Phase Ia powder-in-bottle (PIB) oral solution, 150 mg dose, 48 mg/mL

B—Phase Ib/II powder-in-bottle (PIB) oral solution, 150 mg dose, 48 mg/mL

C—Formulation #1 SGC capsule 1, 150 mg dose

D—Formulation #2 SGC capsule 2, 150 mg dose

E—Formulation #3 HGC capsule, 150 mg dose

Dosing: The Phase Ia and Ib/II PIB oral solutions were formulated with 48 mg/mL of Compound (1) Na salt. Dogs were dosed at a volume of approximately 3.13 mL (150 mg dose) followed by 50 mL of water via gavage. Formulations C, D, and E were formulated to contain 150 mg Compound (1) Na salt in each capsule. Dogs received one capsule followed by 50 mL of water via gavage.

Blood Sampling: Blood samples (~2 ml) were drawn at pre-dose, 0.33, 0.67, 1, 1.5, 2, 3, 4, 6, 8, 12, 24, 30, and 48 hr postdose.

Anticoagulant: Li-Heparin

TABLE 1

Summary of Compound (1) Pharmacokinetic Parameters in Beagle Dogs (n = 6) after Oral Administration of Compound (1) Na salt in Five Different Formulations[a]

| PK Parameter | Formulation | | | | |
|---|---|---|---|---|---|
| | A | B | C | D | E |
| $C_{max}$ (ng/mL) | 6,271 (57) | 6,326 (43) | 7,391 (50) | 10,394 (30) | 8,036 (42) |
| $AUC_{0-48}$ (ng · h/mL) | 33,980 (70) | 33,523 (57) | 45,565 (55) | 57,485 (35) | 43,647 (52) |
| $t_{max}$ (h) | 3 (2-3) | 2 (0.67-2) | 3.5 (1.5-24) | 3 (2-4) | 2.5 (1-4) |

[a]Data are presented as mean (% RSD) except for $t_{max}$ which is presented as median (range). Table includes data from all dogs regardless of emesis.

Figure 2:
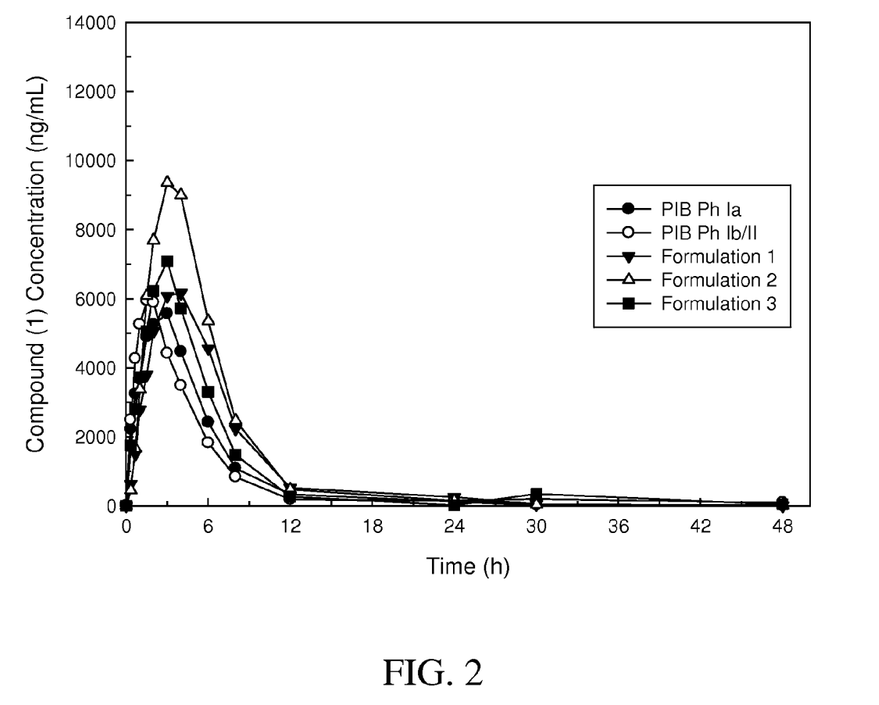
FIG. 2 shows the mean plasma concentrations of Compound (1) in six dogs after dosing with five different formulations of Compound (1) Na salt.

The corresponding mean plasma concentrations of Compound (1) in all dogs after dosing with the five different formulations of Compound (1) Na salt (n=6) is shown in FIG. 2.

TABLE 2

Summary of Compound (1) Pharmacokinetic Parameters in Beagle Dogs (n = 3) after Oral Administration of Compound (1) Na salt in Five Different Formulations[a]

| PK Parameter | Formulation | | | | |
|---|---|---|---|---|---|
| | A | B | C | D | E |
| $C_{max}$ (ng/mL) | 8,315 (35) | 8,416 (21) | 9,846 (19) | 12,744 (15) | 9,707 (30) |

TABLE 2-continued

Summary of Compound (1) Pharmacokinetic Parameters in
Beagle Dogs (n = 3) after Oral Administration of Compound
(1) Na salt in Five Different Formulations[a]

| PK Parameter | Formulation | | | | |
|---|---|---|---|---|---|
| | A | B | C | D | E |
| $AUC_{0-48}$ (ng·h/mL) | 47,336 (58) | 42,623 (35) | 65,399 (25) | 72,894 (16) | 48,214 (11) |
| $t_{max}$ (h) | 3 (2-3) | 2 (1.5-2) | 4 (2-6) | 3 (2-4) | 3 (2-4) |

[a]Data are presented as mean (% RSD) except for $t_{max}$ which is presented as median (range). Table excludes all data for all formulations for dogs that vomited; 1494, 1912, 1916.

Figure 3:
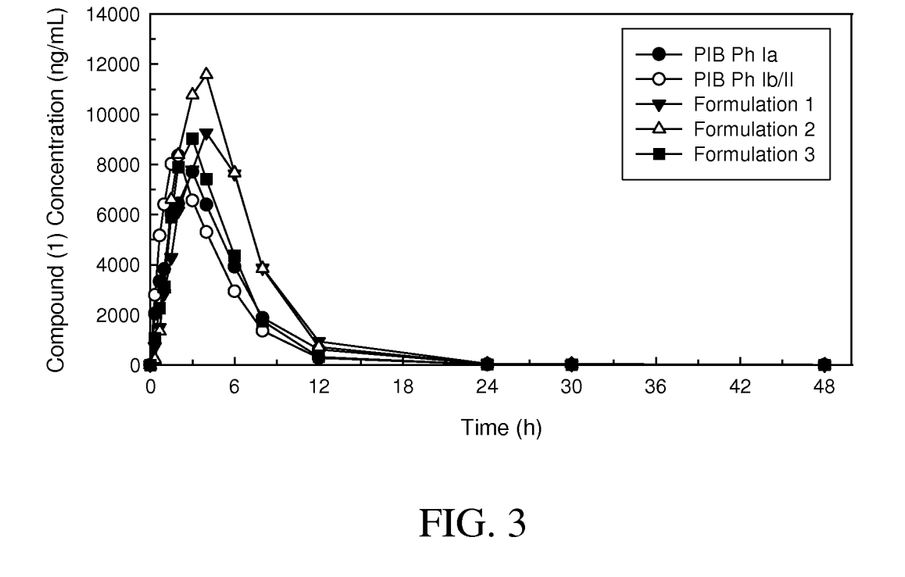
FIG. 3 shows the mean plasma concentrations of Compound (1) in three dogs after dosing with five different formulations of Compound (1) Na salt.

The corresponding mean plasma concentrations of Compound (1) in the three dogs after dosing with the five different formulations of Compound (1) Na salt (n=3) is shown in FIG. 3.

Example 6

Optical Clarity Studies

The optical clarity of formulations of the present invention was observed visually and measured spectroscopically. The fill formulations were prepared according to Formulation #1 (Example 1), as well as corresponding vehicle and placebo formulations, and each diluted to 100 times solutions in three different aqueous media at different pH levels. The absorbance of each solution was measured both immediately and after 30 minutes at 400 nm and 450 nm, using a purified water standard, and the detailed results are provided below. The results demonstrate absorbances of the resulting dispersions in the range of 2.36 to 2.99 at 400 nm 0.35 to 2.96 at 450 nm.

Formulations:

| Target % | Formulation 1 | Vehicle | Placebo |
|---|---|---|---|
| Compound (1) Na salt | 15.0 | — | — |
| Capmul MCM | 46.3 | 54.5 | 61.3 |
| Cremophor EL | 30.8 | 36.2 | 30.8 |
| Alpha-Tocopherol | 0.2 | 0.2 | 0.2 |
| Propylene Glycol | 7.7 | 9.1 | 7.7 |
| Total | 100.0 | 100.0 | 100.0 |

General Procedure:
 Add 0.1 g of formulation sample to 20 mL Scintillation vial
 Add 9.9 mL of aqueous media to vial
 Disperse well by hand mixing
 Measure immediately or let sit for 30 minutes
 Disperse sample before uv reading
 Transfer aliquot to 1 cm path length uv cell
 Absorbance measured as single determination or across range of wavelengths Aqueous Media:
 simulated gastric fluid (SGF)
 acetate buffer
 simulated intestinal fluid (SIF)

Equipment: Cary 50 UV-Vis spectrophotometer
Software: Cary software program "simple reads"
Optical Clarity Results (Time Zero):

| | Absorbance 400 nm | Absorbance 450 nm | Visual Observation at Time Zero |
|---|---|---|---|
| 100x Dilution of Formulation 1 | | | |
| SGF pH 1.2 | 2.94 | 0.38 | Translucent/Clear |
| Acetate Buffer pH 4.5 | 2.62 | 2.46 | Turbid |
| SIF pH 6.8 | 2.60 | 2.46 | Turbid |
| 100x Dilution of Vehicle | | | |
| SGF pH 1.2 | 2.40 | 2.36 | Turbid |
| Acetate Buffer pH 4.5 | 2.36 | 2.31 | Turbid |
| SIF pH 6.8 | 2.45 | 2.39 | Turbid |
| 100x Dilution of Placebo | | | |
| SGF pH 1.2 | 2.61 | 2.48 | Turbid |
| Acetate Buffer pH 4.5 | 2.56 | 2.51 | Turbid |
| SIF pH 6.8 | 2.57 | 2.64 | Turbid |

Optical Clarity Results (30 minutes):

| | Absorbance 400 m | Absorbance 450 nm | Visual Observation after 30 minutes |
|---|---|---|---|
| 100x Dilution of Formulation 1 | | | |
| SGF pH 1.2 | 2.99 | 0.35 | Translucent/Clear |
| Acetate Buffer pH 4.5 | 2.92 | 2.96 | Turbid |
| SIF pH 6.8 | 2.67 | 2.64 | Turbid |
| 100x Dilution of Vehicle | | | |
| SGF pH 1.2 | 2.44 | 2.41 | Turbid |
| Acetate Buffer pH 4.5 | 2.47 | 2.44 | Turbid |
| SIF pH 6.8 | 2.37 | 2.34 | Turbid |
| 100x Dilution of Placebo | | | |
| SGF pH 1.2 | 2.68 | 2.55 | Turbid |
| Acetate Buffer pH 4.5 | 2.48 | 2.41 | Turbid |
| SIF pH 6.8 | 2.50 | 2.42 | Turbid |

Examples 7 to 12

Manufacture of Compound (1) Na Salt

Methods that can be used for preparing amorphous Compound (1) can be found in U.S. Pat. No. 6,323,180, U.S. Pat. No. 7,514,557 and U.S. Pat. No. 7,585,845, which are herein incorporated by reference. Methods that can be used for preparing the sodium salt of Compound (1) may be found in U.S. Patent Application Publication No. 2010/0093792, and in the examples set forth below.

Example 7

Preparation of Type A of Compound (1)

Amorphous Compound (1) (Batch 7, 13.80 g) was added to a 1000 ml three neck flask. Absolute ethanol (248.9 g) was added to the flask. While stirring, the contents of the flask were heated at 60 degrees C./hr to ~74 degrees C. (Solids do not dissolve at 74 degrees C.). Water (257.4 g) was then added linearly over 4 hr to the resulting slurry while stirring and maintaining the temperature at 74 degrees C. After the water addition was complete, the temperature was reduced linearly to ambient temperature at 8 degrees C./hr and then held at ambient temperature for 6 hrs while stirring. The resulting solids were collected by filtration and washed with 50 ml of 1/1 (w/w) EtOH/Water. The wet solids were dried on the funnel for 30 minutes by sucking $N_2$ through the cake. (XRPD analysis on this sample indicates that the pattern is similar to the EtOH solvate). The solids were then dried at 65-70 degrees C. under vacuum (P=25 in Hg) and a nitrogen bleed for 1.5 hr. The resulting solids (12.6 g, 95.5% corrected yield) were confirmed by XRPD as being Type A Compound (1).

Example 8

Preparation of the Sodium Salt of Compound (1)

Method 1

2.1 g of amorphous sodium salt of Compound (1) and 8.90 g of acetone was added to a vial and stirred at ambient temperature for 3 hr. The slurry was filtered off mother liquors and the resulting solids were dried for 20 minutes under nitrogen flow for 20 minutes. 1.51 g of crystalline sodium salt of Compound (1) as solids was collected.

Example 9

Preparation of the Sodium Salt of Compound (1)

Method 2

15.6 g of Type A of Compound (1), 175 ml of acetone and 3.6 ml of water was added to a 250 ml reactor and heated to 53 degrees C. to dissolve the solids. 900 ul of 10.0 N NaOH was added to reactor and the solution was seeded with Type A. The seeded solution was stirred at 53 degrees C. for 10 minutes. A second 900 ul portion of 10.0 N NaOH was added and the system was stirred at 53 degrees C. for 30 minutes over which a slurry developed. The slurry was cooled to 19 degrees C. at a cooling rate of 15 degrees C. per hour and held overnight at 19 degrees C. The final resulting slurry was filtered and the wet solids were washed with 15 ml of acetone. Dried solids for 1 hr at 52 degrees C. under vacuum with a nitrogen flow and then exposed the solids to lab air for one hour. Collected 12.1 g of Compound (1) crystalline sodium salt solids.

Example 10

Preparation of the Sodium Salt of Compound (1)

Method 3

25.4 Kg of amorphous Compound (1), 228 L of THF and 11.1 Kg of 10 wt % NaOH (aq) was added to a reactor. The components were mixed at 25 degrees C. to dissolve all solids. The resulting solution was filtered and the reactor and filter was washed with 23 L of THF. 180 L of solvent was removed using atmospheric distillation at 65 degrees C. 195 L of MIBK was added and 166 L of solvent was removed by vacuum distillation at ~44 degrees C. 161 L of MIBK and 0.41 Kg of water was added back to the reactor and the contents were heated to 70 degrees C. 255 g of Compound (1) sodium salt seeds were added at 70 degrees C. and 1.42 L of water was added over 1.5 hours. After the water addition the slurry was held at 70 degrees C. for 45 minutes and then cooled to 45 degrees C. over 1 hr. The resulting slurried was filtered and washed with 64 L of MIBK containing ~0.8 weight % water. The wet cake was dried at 55 degrees C. to give ~25 Kg of crystalline sodium salt of Compound (1).

Example 11

Preparation of the Sodium Salt of Compound (1)

Method 4

2.00 g of amorphous Compound (1), 9.96 g of THF and 0.11 g of water was added to a reactor and stirred at ambient temperature to dissolve solids. 0.820 ml of 21 weight % NaOEt in ethanol was added drop-wise while stirring the solution to get solution A. 15.9 g of n-BuAc and 160 ul of water was added to a second reactor and heated to 65 degrees C. (solution B). 2.56 g of Solution A was added to Solution B at 65 degrees C. and the resulting mixture was seeded with 40 mg of Compound (1) sodium salt seeds. The seeded mixture was aged at 65 degrees C. for 45 minutes. 2.56 g of Solution B was added to Solution A and aged for 45 minutes in four separate intervals. After the final addition and aging, the slurry was cooled to 50 degrees C. over 1 hour and filtered. The wet cake was washed with 6 ml of n-BuAc containing 0.5 weight % water. The final solids were dried at 50 degrees C. under vacuum using a nitrogen purge. Compound (1) crystalline sodium salt solids were collected.

Example 12

Preparation of the Sodium Salt of Compound (1)

Method 5

At room temperature a solution of sodium ethoxide in ethanol (21 weight %; 306 ml) was added to a solution of Compound (1) (745 g) in THF (2000 ml) and water (76.5 ml) while stirring. After stirring for 30 minutes, the mixture was filtered and the filter was washed with THF (85 ml). The resulting solution was warmed to 65° C. and treated with filtered butyl acetate (6640 ml, optionally pre-warmed to 65° C.) within 30 minutes. Seeding crystals (0.50 g) were added, and the mixture was stirred at 65° C. for 2 hours, while crystallization starts after about 30 minutes. The suspension was cooled to 50° C. within 1 hour and stirred at this temperature for an additional hour. The title compound was isolated by filtration, washed with filtered butyl acetate (765 ml, optionally pre-warmed to 50° C.) and dried at 65° C. for about 16 h giving Compound (1) crystalline sodium salt (~725 g).

We claim:
1. A liquid pharmaceutical composition comprising:
(a) a compound of formula (1):

or a pharmaceutically acceptable salt thereof;
(b) one or more pharmaceutically acceptable lipids; and
(c) one or more pharmaceutically acceptable hydrophilic surfactants;
wherein upon dilution with an aqueous solution at an aqueous solution to composition ratio of 100:1 by weight, the composition forms an aqueous dispersion having an absorbance of more than about 1.0 at a wavelength of about 400 nm.

2. The pharmaceutical composition according to claim 1, wherein the compound of formula (1) is present as the sodium salt.

3. The pharmaceutical composition according to claim 1, wherein the compound of formula (1) or the pharmaceutically acceptable salt thereof is present in an amount of 1 to 50% by weight.

4. The pharmaceutical composition according to claim 1, wherein the one or more pharmaceutically acceptable lipids are present in an amount of from about 20% to 70% by weight.

5. The pharmaceutical composition according to claim 1 or 4, wherein the one or more pharmaceutically acceptable lipids are selected from: fatty acids, medium chain monoglycerides, medium chain diglycerides, medium chain triglycerides, long chain monoglycerides, long chain diglycerides, long chain triglycerides, propylene glycol fatty acid esters, sorbitol fatty acid esters, water insoluble vitamins, and mixtures thereof.

6. The pharmaceutical composition according to claim 1, wherein the one or more pharmaceutically acceptable hydrophilic surfactants are present in an amount of up to about 70% by weight.

7. The pharmaceutical composition according to claim 1 or 6, wherein the one or more pharmaceutically acceptable hydrophilic surfactants are selected from: polyethoxylated vegetable oils, polyethoxylated tocopherols, polyethoxylated sorbitol fatty acid esters, bile salts, lecithins, and mixtures thereof.

8. The pharmaceutical composition according to claim 1, further comprising a pharmaceutically acceptable hydrophilic solvent.

9. The pharmaceutical composition according to claim 8, wherein the pharmaceutically acceptable hydrophilic solvent is selected from: propylene glycol, polypropylene glycol, polyethylene glycol, glycerol, ethanol, dimethyl isosorbide, glycofurol, propylene carbonate, dimethyl acetamide, water, and mixtures thereof.

10. The pharmaceutical composition according to claim 8 or 9, wherein the pharmaceutically acceptable hydrophilic solvent is present in an amount of up to 30% by weight.

11. The pharmaceutical composition according to claim 1, comprising:
(a) about 5% to 30% by weight of the compound of formula (1) or the pharmaceutically acceptable salt thereof;
b) about 30% to 60% by weight of the one or more pharmaceutically acceptable lipids;
(c) about 20% to 50% by weight of the one or more pharmaceutically acceptable hydrophilic surfactants; and
(d) optionally up to about 30% by weight of a pharmaceutically acceptable hydrophilic solvent.

12. The pharmaceutical composition according to claim 1, comprising:
(a) about 10% to 20% by weight of the compound of formula (1) or the pharmaceutically acceptable salt thereof;
(b) about 40% to 50% by weight of the one or more pharmaceutically acceptable lipids;
(c) about 25% to 35% by weight of the one or more pharmaceutically acceptable hydrophilic surfactants; and
(d) about 5% to 15% by weight of a pharmaceutically acceptable hydrophilic solvent.

13. The pharmaceutical composition according to claim 1, comprising:
(a) about 5% to 30% by weight of the compound of formula (1) or the pharmaceutically acceptable salt thereof;
(b) about 30% to 60% by weight of the one or more pharmaceutically acceptable lipids, wherein the one or more pharmaceutically acceptable lipids are selected from: fatty acids, medium chain monoglycerides, medium chain diglycerides, medium chain triglycerides, long chain monoglycerides, long chain diglycerides, long chain triglycerides, propylene glycol fatty acid esters, sorbitol fatty acid esters, water insoluble vitamins, and mixtures thereof;
(c) about 20% to 50% by weight of the one or more pharmaceutically acceptable hydrophilic surfactants, wherein the one or more pharmaceutically acceptable hydrophilic surfactants are selected from: polyethoxylated vegetable oils, polyethoxylated tocopherols, polyethoxylated sorbitol fatty acid esters, bile salts, lecithins, and mixtures thereof; and
d) optionally up to about 30% by weight of a pharmaceutically acceptable hydrophilic solvent selected from: propylene glycol, polypropylene glycol, polyethylene glycol, glycerol, ethanol, dimethyl isosorbide, glycofurol, propylene carbonate, dimethyl acetamide, water, and mixtures thereof.

14. The pharmaceutical composition according to claim 1, comprising:
(a) about 10% to 20% by weight of the compound of formula (1) as the sodium salt form;
(b) about 40% to 50% by weight of the one or more pharmaceutically acceptable lipids, wherein the one or more pharmaceutically acceptable lipids are selected from:

monoglycerides of caprylic and capric fatty acids, diglycerides of caprylic and capric fatty acids, and mixtures thereof;

(c) about 25% to 35% by weight of the one or more pharmaceutically acceptable hydrophilic surfactants, wherein the one or more pharmaceutically acceptable surfactants are selected from: tocopheryl polyethylene glycol succinate, polyoxyl 40 hydrogenated castor oil, and polyoxyl 35 castor oil, and mixtures thereof; and (d) about 5% to 10% by weight of a pharmaceutically acceptable hydrophilic solvent selected from propylene glycol, polyethylene glycol, ethanol, water, and mixtures thereof.

15. The pharmaceutical composition according to claim 1, which is either substantially free of any amine compound, or not containing any amine compound.

16. The pharmaceutical composition according to claim 1, which is either substantially free of any alcohol compound, or not containing any alcohol compound.

17. The pharmaceutical composition according to claim 1, which is either substantially free of any triglyceride, or not containing any triglyceride.

18. The pharmaceutical composition according to claim 1, which is either substantially free of any glyceride of a long chain fatty acid, or not containing any such glyceride.

19. The A pharmaceutical composition according to claim 1, which is either substantially free of any additional surfactant compound, or not containing any additional surfactant compound, other than the one or more pharmaceutically acceptable hydrophilic surfactants recited in claim 1.

\* \* \* \* \*